United States Patent
Hoffmann

[11] Patent Number: 6,048,299
[45] Date of Patent: Apr. 11, 2000

[54] RADIATION DELIVERY CATHETER

[75] Inventor: Gerard von Hoffmann, Trabuco Canyon, Calif.

[73] Assignee: Radiance Medical Systems, Inc., Irvine, Calif.

[21] Appl. No.: 08/965,900

[22] Filed: Nov. 7, 1997

[51] Int. Cl.$^7$ ............................................. A61N 5/00
[52] U.S. Cl. .................................... 600/3; 604/281
[58] Field of Search .......................... 600/1–8; 604/19, 604/280, 281, 282

[56] References Cited

U.S. PATENT DOCUMENTS

| | | |
|---|---|---|
| 3,324,847 | 6/1967 | Zoumboulis . |
| 4,115,536 | 9/1978 | Rothman et al. . |
| 4,124,705 | 11/1978 | Rothman et al. . |
| 4,126,669 | 11/1978 | Rothman et al. . |
| 4,225,790 | 9/1980 | Parsons, Jr. et al. . |
| 4,423,725 | 1/1984 | Baran et al. . |
| 4,581,017 | 4/1986 | Sahota . |
| 4,588,395 | 5/1986 | Lemelson . |
| 4,655,771 | 4/1987 | Wallsten . |
| 4,674,480 | 6/1987 | Lemelson . |
| 4,706,652 | 11/1987 | Horowitz . |
| 4,762,129 | 8/1988 | Bonzel . |
| 4,815,449 | 3/1989 | Horowitz . |
| 4,819,618 | 4/1989 | Liprie . |
| 4,878,492 | 11/1989 | Sinofsky et al. . |
| 5,011,677 | 4/1991 | Day et al. . |
| 5,019,369 | 5/1991 | Presant et al. . |
| 5,040,548 | 8/1991 | Yock . |
| 5,059,166 | 10/1991 | Fischell et al. . |
| 5,061,273 | 10/1991 | Yock . |
| 5,106,360 | 4/1992 | Ishiwara et al. . |
| 5,176,617 | 1/1993 | Fischell et al. . |
| 5,199,939 | 4/1993 | Dake et al. . |
| 5,213,561 | 5/1993 | Weinstein et al. . |
| 5,267,960 | 12/1993 | Hayman et al. . |
| 5,302,168 | 4/1994 | Hess . |
| 5,302,369 | 4/1994 | Day et al. . |
| 5,354,257 | 10/1994 | Roubin et al. . |
| 5,411,466 | 5/1995 | Hess . |

(List continued on next page.)

FOREIGN PATENT DOCUMENTS

| | | |
|---|---|---|
| WO 93/04735 | 3/1993 | WIPO . |
| WO 94/23789 | 10/1994 | WIPO . |
| WO 95/19807 | 7/1995 | WIPO . |
| WO 95/29008 | 11/1995 | WIPO . |
| WO 96/10436 | 4/1996 | WIPO . |
| WO 96/13303 | 5/1996 | WIPO . |
| WO 96/14898 | 5/1996 | WIPO . |
| WO 96/22121 | 7/1996 | WIPO . |
| WO 97/18012 | 5/1997 | WIPO . |

OTHER PUBLICATIONS

*Radiation Quantities and Units.* ICRU Report 33, International Commission on Radiation, Units and Measurements, Apr. 15, 1980.

(List continued on next page.)

*Primary Examiner*—John P. Lacyk
*Attorney, Agent, or Firm*—Knobbe, Martens, Olson & Bear, LLP

[57] ABSTRACT

Disclosed is a delivery catheter adapted for delivery of a dose of radiation to a vessel wall. A radiation source is enlargeable from a first, reduced cross-sectional profile to a second, enlarged cross-sectional profile by unwinding around a central core. Following delivery of a radiation dose to the vessel wall, the source is reduced in profile by wrapping around the core and removed from the treatment site.

34 Claims, 2 Drawing Sheets

U.S. PATENT DOCUMENTS

| | | |
|---|---|---|
| 5,424,288 | 6/1995 | Order . |
| 5,484,384 | 1/1996 | Fearnot . |
| 5,498,227 | 3/1996 | Mawad . |
| 5,503,613 | 4/1996 | Weinberger . |
| 5,540,659 | 7/1996 | Tierstein . |
| 5,605,530 | 2/1997 | Fischell et al. . |
| 5,616,114 | 4/1997 | Thornton et al. . |
| 5,618,266 | 4/1997 | Liprie . |
| 5,643,171 | 7/1997 | Bradshaw et al. . |
| 5,653,683 | 8/1997 | D'Andrea . |
| 5,662,580 | 9/1997 | Bradshaw et al. . |
| 5,674,177 | 10/1997 | Hehrlein et al. . |
| 5,683,345 | 11/1997 | Waksman et al. . |
| 5,688,220 | 11/1997 | Verin et al. . |
| 5,707,332 | 1/1998 | Weinberger . |
| 5,713,828 | 2/1998 | Coniglione . |
| 5,720,717 | 2/1998 | D'Andrea . |
| 5,722,984 | 3/1998 | Fischell et al. . |
| 5,723,003 | 3/1998 | Winston et al. . |
| 5,728,042 | 3/1998 | Schwager . |
| 5,730,698 | 3/1998 | Fischell et al. . |
| 5,755,690 | 5/1998 | Saab . |
| 5,762,631 | 6/1998 | Klein . |
| 5,782,740 | 7/1998 | Schneiderman . |
| 5,782,741 | 7/1998 | Bradshaw et al. . |
| 5,782,742 | 7/1998 | Crocker et al. . |
| 5,795,286 | 8/1998 | Fischell et al. . |
| 5,863,284 | 1/1999 | Klein . |
| 5,871,436 | 2/1999 | Eury . |
| 5,879,282 | 3/1999 | Fischell et al. . |

OTHER PUBLICATIONS

*Effects of high–dose intracoronary irradiation on vasomotor function and smooth muscle histopathology,* Joseph G. Wiedermann, Jeffrey A. Leavy, Howard Amols, Allan Schwartz, Shunichi Homma, Charles Marboe and Judah Weinberger, Interventional Cardiology Center, Department of Medicine and Radiation Oncology and Section of Cardiac Pathology, Columbia–Presbyterian Medical Center and Columbia University, 1994 the American Physiological Society.

*Intracoronary Irradiation Markedly Reduces Restenosis After Balloon Antioplasty in a Porcine Model,* Joseph G. Weidermann, MD, Charles Marboe, MD, Howard Amols, PhD, Allan Schwartz, MD, FACC, Judah Weinberger, MD, PhD, FACC, JACC vol. 23. No. 6, May 1994:1491–8.

*Intracoronary Irradiation Markedly Reduces Neointimal Proliferation After Balloon Angioplasty in a Swine*: Persistent Benefit at 6–Month Follow–up, Joseph G. Wiedermann, MD, Charles Marboe, MD, Howard Amols, PhD, Allan Schwartz, MD, FACC, Judah Weinberger, MD, PhD, FACC, JACC vol. 25. No. 6, May 1995:1451–6.

*Discoveries in Radiation for Restenosis,* Emory University of School of Medicine, Presented by The Andreas Gruentzig Cardiovascular Center and the Department of Radiation Oncology of Emory University School of Medicine; J.W. Marriott Hotel at Lenox, Atlanta, Ga, Jan. 11–12, 1996.

Radioactive Balloon Catheter to Inhibit Restenosis after Angioplasty.

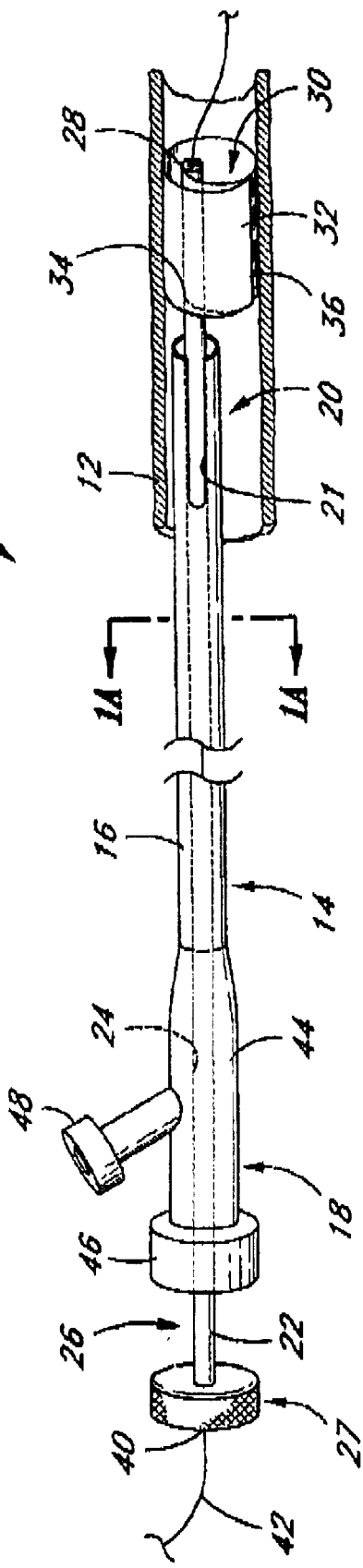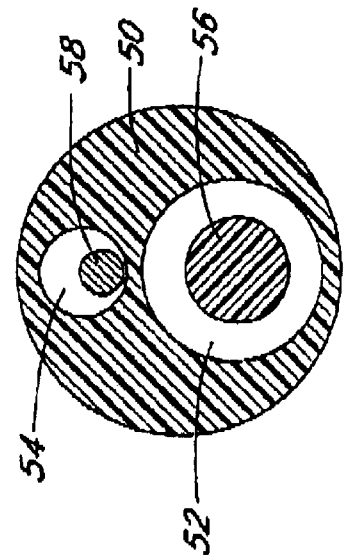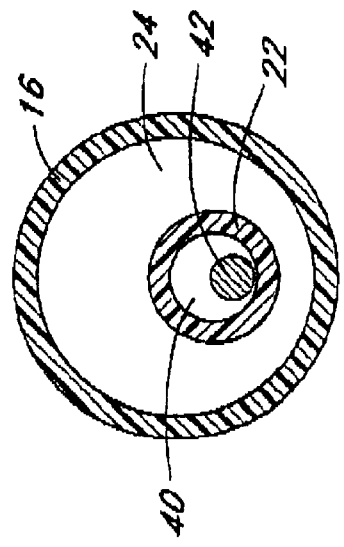

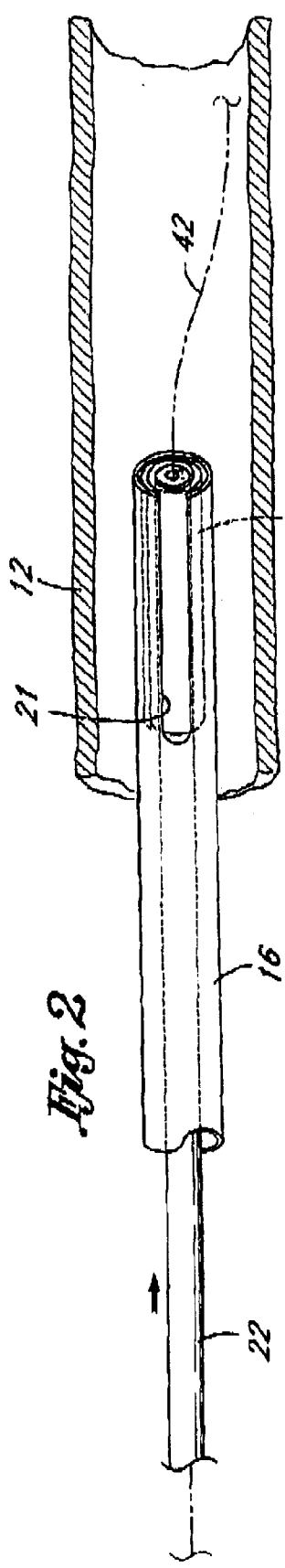
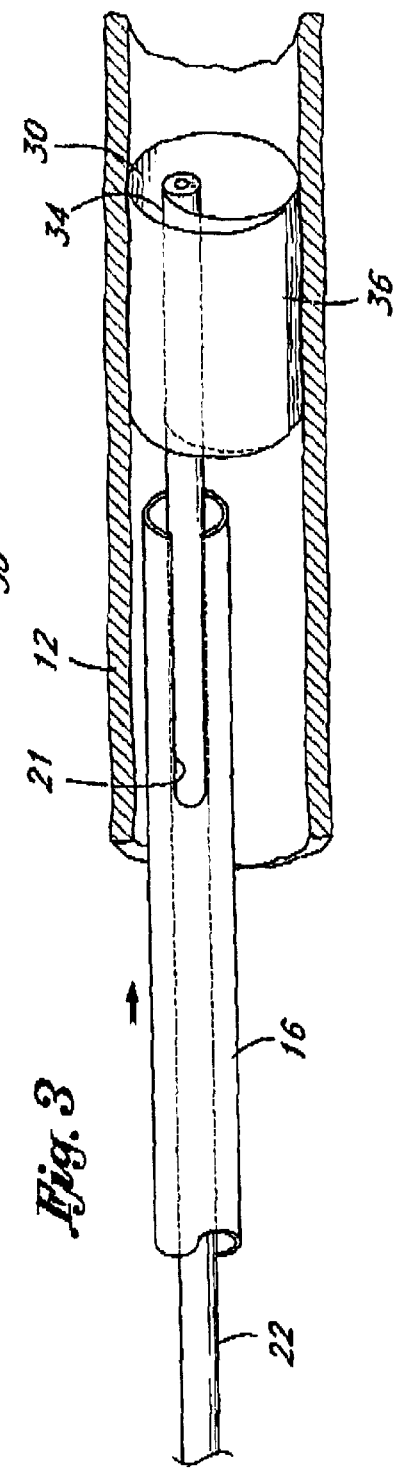
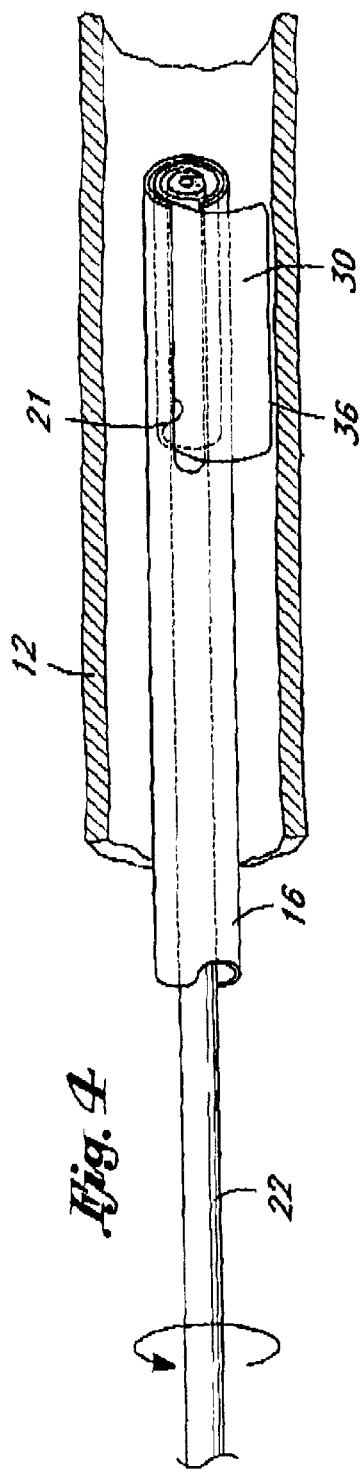

RADIATION DELIVERY CATHETER

BACKGROUND OF THE INVENTION

This invention relates to catheters useful to deliver radiation to prevent or slow restenosis of an artery traumatized such as by percutaneous transluminal angioplasty (PTA).

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States in 1990 and nearly one million procedures worldwide in 1997. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% or more of all patients requiring repeat PTCA procedures or by-pass surgery, with attendant high cost and added patient risk.

More recent attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to slow the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or other procedure to alleviate the restenosis.

Preliminary studies indicate that intravascular radiotherapy (IRT) has promise in the prevention or long-term control of restenosis following angioplasty. IRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation and hemorrhaging. Underdosing will result in inadequate inhibition of smooth muscle cell hyperplasia, or even exacerbation of hyperplasia and resulting restenosis.

U.S. Pat. No. 5,059,166 to Fischell discloses an IRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. In addition, current stents are generally not removeable without invasive procedures. The dose delivered to the blood vessel is also non-uniform because the tissue that is in contact with the individual strands of the stent receive a higher dosage than the tissue between the individual strands. This non-uniform dose distribution may be especially disadvantageous if the stent incorporates a low penetration source such as a beta emitter.

U.S. Pat. No. 5,302,168 to Hess teaches the use of a radioactive source contained in a flexible carrier with remotely manipulated windows. H. Böttcher, et al. of the Johann Wolfgang Goerhe University Medical Center, Frankfurt, Germany report in November 1992 of having treated human superficial femoral arteries with a similar endoluminal radiation source. These radioactive wire type methods generally require use of a relatively high activity source to deliver an effective dose. Accordingly, measures must be taken to ensure that the source is maintained reasonably near the center of the lumen to prevent localized overexposure of tissue to the radiation source. Use of these higher activity sources also dictates use of expensive shielding and other equipment for safe handling of the source.

Despite the foregoing, among many other advances in IRT, there remains a need for an IRT method and apparatus that delivers an easily controllable uniform dosage of radiation to the walls of the blood vessel without the need for special devices or methods to center a radiation source in the lumen, the need for expensive shielding to protect medical personnel, or the need for expensive remote afterloaders to handle the higher activity sources. Preferably, the apparatus provides a removable radiation source, and permits perfusion during the treatment period.

SUMMARY OF THE INVENTION

There is provided in accordance with one aspect of the present invention a radiation delivery catheter for temporarily placing a radiation source adjacent a vessel wall. The delivery catheter comprises an elongate, flexible tubular body, having a proximal end and a distal end. An axially and rotationally moveable core having proximal and distal ends extends through the tubular body. At least one flexible metal sheet is disposed on the distal end of the core, such that the metal sheet is moveable between a first position within the tubular body and a second position outside the tubular body. Preferably, the metal sheet is rolled into a tube having a reduced diameter when in the first position, and the tube self expands by at least partially unrolling into a larger diameter adjacent the vessel wall when the sheet is in the second position.

In accordance with another aspect of the present invention, there is provided a radiation delivery catheter. The delivery catheter comprises a first elongate element, having a proximal end and a distal end. A second elongate element is moveable with respect to the first element, and a radiation source is attached to the second element. Rotation of one end of the radiation source with respect to another end causes the source to change from a reduced cross sectional area to an enlarged cross sectional area. In one embodiment, the radiation source comprises a flexible metal sheet which is rolled into a first, reduced diameter tubular configuration for positioning at a treatment site in the vessel, and biased towards a second, larger diameter tubular configuration for contacting the vessel wall.

In accordance with a further aspect of the present invention, there is provided a radiation delivery catheter having an elongate flexible tubular body with proximal and distal ends. A self expandable, circumferentially rolled radiation delivery source is provided on the distal end of the catheter. In one embodiment, the radiation delivery source comprises a thin metal sheet rolled into a tubular configuration. In another embodiment, the delivery source comprises a plurality of circumferentially extending ribbons or wires.

In accordance with a further aspect of the present invention, there is provided a method of delivering a dose of radiation to a site in a vessel or body cavity. The method comprises the steps of providing a radiation delivery catheter having a self expandable radiation source on a distal end thereof. The radiation source is positioned at the site, and permitted to self expand at the site. The radiation source is permitted to remain at the site for a radiation delivery period, and thereafter the radiation source is radially reduced and withdrawn from the site. The radiation source self expands by permitting at least one rolled flexible metal element to partially unroll from a reduced cross sectional area for positioning at the site to an enlarged cross sectional area for treating the site. Preferably, the step of radially reducing the radiation source comprises winding the radiation source around a rotatable core wire. The positioning the radiation source at the site step may comprise positioning the radiation source within a vessel following balloon angioplasty, or positioning the source within a previously implanted stent Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a schematic side elevational view of a delivery catheter of the present invention illustrated in a delivery profile within a vessel.

FIG. 1A is a cross-sectional view taken along the lines 1A—1A of FIG. 1.

FIG. 1B is an alternate cross-sectional view of the catheter of FIG. 1, showing a side-by-side lumen configuration.

FIG. 2 is a partial side elevational view of the distal end of the device of FIG. 1, with the delivery structure in a reduced cross-sectional profile such as for placement within a vessel.

FIG. 3 is a side elevational view as in FIG. 2, with the delivery structure in the enlarged, delivery profile.

FIG. 4 is a side elevational view as in FIG. 2, with the delivery structure in the process of reduction from the delivery profile to the reduced profile.

DETAILED DESCRIPTION OF THE PREFERRED EMBODIMENTS

The present invention provides a delivery catheter for delivery by direct or proximate contact between a delivery structure and the wall of a lumen, potential lumen, or body cavity. In one embodiment, the delivery catheter is useful for delivering radiation to the wall of a vessel such as an artery. Alternatively, the delivery structure may deliver any of a wide variety of drugs which are transportable by direct or proximate contact, such as by diffusion, migration, or other mechanisms as may be appropriate for the drug or carrier as will be appreciated by those of skill in the art.

Referring to FIG. 1, there is illustrated a delivery catheter 10 schematically illustrated as positioned within a vessel 12. Although any of a wide variety of applications will become apparent to those of skill in the art in view of the disclosure herein, one particular application of the present invention is for use in delivering radiation to a vessel such as an artery. Radiation delivery to the artery may be accomplished in the region of a stenosis either before or following a transvascular recanalization procedure. Any of a variety of recanalization procedures may benefit from post-procedure irradiation, including balloon angioplasty, rotational aetherectomy, and others as will be apparent to those of skill in the art. The device of the present invention is also useful for delivering radiation within a stent or graft, such as immediately following stent placement (e.g., within minutes to a few days of the initial procedure), or as a later follow-up treatment for in-stent or in-graft restenosis months or years later. Mid-graft locations, anastomoses or other vascular injury sites of varying etiology may also benefit from the present invention.

The delivery catheter 10 comprises an elongate flexible body 14 having a diameter, length and flexibility appropriate to reach the desired treatment site. Preferably, the flexible body 14 comprises a tube 16 having a proximal end 18 and a distal end 20. Tube 16 may comprise any of a variety of metal, metal reinforced polymer or polymeric materials. For example, extruded high density polyethylene, polytetrafluoroethylene, nylons, PEBAX and others are well known in the art.

For most applications the tube 16 has an outside diameter within the range of from about 0.018 inches to about 0.065 inches. For coronary vascular applications, the OD of the tubular body 16 is typically within the range of from about 0.020 to about 0.045 inches. The length of the tubular body 16 for use in coronary applications accessed by a femoral puncture will typically be in the range of from about 120 cm to about 140 cm. Wall thicknesses on the order of 0.003 inches for small vessel catheters on up to about 0.008 inches or greater for larger vessel catheters may be used. Dimensions and materials for any particular catheter can be readily optimized by persons of skill in the art in view of the intended use of the catheter.

An elongate core 22 extends axially through the flexible body 14 by way of a lumen 24. The core 22 is provided with a proximal end 26 which is generally accessible at the proximal end of the delivery catheter 10, and a distal end 28. The core 22 may comprise a solid rod or tubular member, made from stainless steel or any of a variety of other metals well known in the invasive medical device art. Alternatively, any of a wide variety of polymeric materials such as high density polyethylene, nylon, polyimide and others known in the art may be used. A variety of woven or braided multilayer tubular elements may be used for the core 22. In general, the core 22 may comprise any of a variety of structures or materials which provide sufficient torque transmission for winding the radioactively chargeable delivery element 30 as will be discussed. In addition, in the illustrated embodiment, the core 22 should have sufficient column strength to permit the radioactively chargeably delivery element 30 to be displaced distally from the distal end 20 of the flexible body 14.

The distal end 28 of the core 22 is removably or permanently secured to a radioactively chargeable delivery element 30. In the illustrated embodiment, the delivery element 30 comprises a solid or apertured flexible sheet 32 which has a first edge 34 secured to the core 32 and a second edge 36 on the opposite side of the sheet from the first edge 34. In this manner, rotation of the core 22 allows the flexible sheet 32 to be rolled up around the core 22, to assume a low profile such as for retraction into the central lumen 24 of the flexible body 14. Attachment may be accomplished such as by soldering, brazing, or other techniques depending upon the materials of the core 22 and sheet 32.

The delivery element 30 may have an axial (parallel to the axis of the catheter) length anywhere within the range of from about one-half centimeters to about 20 centimeters. Intermediate lengths such as 2 cm, 5 cm, 10 cm or 15 cm may also be provided to treat long lesions or other long treatment sites. In an embodiment where the delivery element 30 comprises a single sheet throughout the axial length of the delivery element 30, the single sheet will generally have an axial length within the range of from about one-half a centimeter or less to no more than about two or three centimeters. Axial lengths of a single rolled sheet in excess of this amount will find relatively limited applications, due to the relative lack of lateral flexibility. In an embodiment intended for use in the coronary artery or other tortuous anatomy, axial lengths of no more than about 1 or 1.5 centimeters will generally be utilized.

Increased lateral flexibility of the delivery element 30 can be achieved by constructing the delivery element 30 as a plurality of flexible wires or ribbons axially adjacent each other along the length of the delivery zone. Such ribbons may have a width measured in the axial direction anywhere within the range from about 0.5 millimeter or less to about 5 millimeters or more, depending upon the desired flexibility characteristics.

In addition to improving the flexibility of the delivery zone, the provision of a plurality of narrow (e.g., 1 mm–5 mm) width ribbons allows the delivery element 30 to more closely conform to the vessel wall when in the enlarged, delivery profile. In an embodiment where the delivery structure comprises a single expandable sheet 32, the sheet will tend to radially expand when released from the catheter 10 to assume a generally cylindrical configuration. Thus, in a vessel having an irregular interior topography, the flexible sheet 32 may expand only to the narrowest luminal diameter within the treatment site. The provision of a plurality of wires or ribbons adjacent each other along the length of the delivery zone will allow each individual wire or ribbon to radially expand to the greatest extent possible at its unique axial position within the treatment zone. Thus, the delivery element 30 will more closely conform to the vessel wall. This may be important if the delivery element 30 is utilized to transmit a relatively low energy radiation source (e.g., beta radiation) which has a relatively low depth of penetration as will be understood to those of skill in the art.

In a preferred embodiment, the delivery element 30 comprises a generally rectangular sheet having a first edge 34 for alignment parallel to the axial direction of the catheter 10. The sheet comprises a flexible material having sufficient resilience that it can be rolled tightly around the core 22 and will tend to unroll into a larger tubular configuration under its own bias upon release of a restraint such as by retraction of the wall of the tubular body 16. The sheet is thus similar in some respect to the rolled stent disclosed in U.S. Pat. Nos. 5,306,294 and 5,411,551 both to Winston et al., the disclosures of which are incorporated in their entirety herein by reference.

For drug delivery applications, the sheet may comprise any of a variety of impregnable polymers, such as polymers having interstitial spaces for entrapping medication which will gradually disperse into the adjacent vessel wall following catheter placement. Alternatively, medication can be bound to the surface of the sheet such as by a bond which can be broken in the aqueous environment of the blood vessel. In this manner, the substance to be delivered can be delivered through direct contact with the vessel wall at the desired delivery site, without interrupting perfusion during the delivery period.

For radiation delivery applications, the sheet comprises one or more radioisotopes or other radiation source materials. Metals such as stainless steel or Elgiloy may be used. Nitinol may also be used, although extra measures must be taken to retain a radioactive charge as is understood in the radioactive stent arts. The thickness of the sheet can be optimized in view of the particular sheet material and catheter design, but for certain metals will generally be on the order of no more than about 0.001 inches, preferably no more than about 0.0005 inches or possibly less.

The length of the sheet from first edge 34 to second edge 36 is preferably at least about as long as the circumference of the vessel or other lumen or cavity at the desired target site. Thus, a sheet having a circumferential length of at least about 9.5 mm will preferably be used in a catheter intended for radiation delivery to a 3 mm vessel to ensure continuous circumferential radiation delivery. Sheet lengths in the range of from about 6 mm to about 30 mm or greater may be used depending upon the intended target.

Although multiple overlaps of the sheet in the enlarged profile may be used as described in the '294 and '551 patents to Winston, et al., that is not necessary since the delivery element 30 needs only sufficient radial force to provide direct contact with the vessel wall. Circumferential length of the sheet greatly in excess of a single circumference of the treatment site may unnecessarily increase the minimum insertion profile of the catheter 10, and lengthen or otherwise complicate the process of retracting the sheet into the catheter following the desired delivery period.

A ribbon embodiment of the delivery element 30 may be conveniently be prepared by selecting an appropriate sheet size as described above and providing a plurality of spaced apart parallel cuts in the circumferential direction to provide a plurality of parallel ribbons. The cuts may extend from second edge 36 at least about 75% and preferably at least about 85% or 95% of the way to the first edge 34 to leave a backbone for securing the first edge 34 to the core 32. The first edge 34 of any of the above embodiments may then be secured to the core as has been described, such as by soldering. In addition, interference fit or interlocking relationships can be used to enhance the integrity of the bond. For example, the first edge 34 can be wrapped all the way around the core and soldered to itself as well as to the core. Alternatively, the core can be provided with an axially extending slot for receiving a portion of e sheet therein.

In the illustrated embodiment, the core 22 is provided with a central guidewire lumen 40, for axially slidably receiving a conventional guidewire 42. The proximal end 18 of delivery catheter 10 is provided with a manifold 44 which can be injection molded from any of a variety of medical grade plastics as is well understood in the art. The manifold 44 is preferably provided with at least one access port 46, for sealingly receiving the core 22 therethrough. Access port 46 is preferably provided with an internal septum or other sealing structure (not illustrated) as is understood in the art.

The manifold 44 may additionally be provided with a side port 48, having a side port lumen in fluid communication with the central lumen 24 of the delivery catheter 10. Side port 48 can thus be utilized for any of a variety of purposes, such as the infusion of anticoagulants or other medications or fluids, including radio opaque dye for the purpose of visualization of the treatment site during the placement, delivery and removal procedures. Preferably, the proximal end 26 of the core 22 is additionally provided with a control 27, such as a knurled knob or wheel which permits the clinician to conveniently rotate the core 22 as well as axially displace the core 22 as may be desired during the deployment and retraction steps. Alternatively, any of a variety of controls 27 may be readily adapted for use with the delivery catheter 10 of the present invention, including electronically driven rotational and axial advancement and replacement mechanisms.

Referring to FIG. 1B, there is illustrated an alternate, side-by-side configuration for the delivery catheter 10. In this embodiment, the body 50 may be extruded as a dual lumen side-by-side configuration, having a first lumen 52 and a second lumen 54. The core 56 is axially and rotationally moveably positioned within the first lumen 52, and the guidewire 58 is movably positioned within the second lumen 54. The proximal end of the guidewire lumen 54 can extend all the way to a port at the manifold 44, or can extend to a side port positioned along the side of the flexible body 14 such as within about 20 cm of the distal end 20 in a rapid exchange embodiment. In both the FIG. 1A (coaxial) and FIG. 1B (side-by-side) illustrations, the drawings are not to scale. Thus, the relative diameters of the various lumen and structures can be modified, depending upon whether additional lumen volume is desired such as for infusion of media or whether the outside diameter of the catheter is preferably minimized as will be understood by those of ordinary skill in the art.

Referring to FIG. 2, the delivery catheter 10 is illustrated in the reduced cross-sectional profile. This configuration is useful for percutaneous insertion and transluminal advancement to a treatment site. Once the distal end 20 of the catheter is positioned at a desired treatment site, the core 20 is axially distally advanced with respect to the delivery catheter 10. Axial relative advancement can be accomplished either by advancing the core 22 distally or by retracting the delivery catheter 10 proximally depending upon the preferred mode for a given application. In general, proximal retraction of the delivery catheter 10 with respect to the core 22 may be desirable because it may minimize the likelihood of intimal injury due to the distal edge of the rolled flexible sheet 32.

Once the flexible sheet 32 or other delivery element 30 has been positioned distally of the tubular body 14, the flexible sheet 32 preferably unrolls under its own bias as illustrated in FIG. 3 to position adjacent the vessel wall. The delivery sheet 32 may then be left in an expanded tubular configuration adjacent the vessel wall for the duration of the desired treatment. Advantageously, the enlarged profile of the present invention permits perfusion through the central lumen of the tubular expanded delivery sheet 32, thereby permitting extended delivery periods as may be desirable for certain radiation or drug delivery treatments.

Following the desired delivery time, the delivery element 30 is retracted within the central lumen 24 of the delivery catheter 10. This may be accomplished by rotating the control 27 thereby winding the flexible sheet 32 around the core 22 to reduce the sheet to its reduced cross-sectional configuration. To facilitate winding of the flexible sheet 32 around the core 22, a slot 21 may be provided at the distal end of the tubular body 16. Axial distal advancement of the delivery catheter 10 with rotation of the delivery catheter and/or the core 22 will permit the first end 34 of the sheet 32 to be rotationally aligned with and axially drawn into the slot 21. This will permit rotation of the core 22 with respect to the delivery catheter 10 to wind the sheet around the core as is illustrated in FIG. 4. Following retraction of the flexible sheet 32 within the delivery catheter 10, the catheter 10 can be removed from the treatment site in accordance with conventional post catheterization techniques.

In its application as a radiation delivery catheter, any of a wide variety of radio isotopes can be utilized, depending upon the desired radiation source. Although clinical research is ongoing concerning the desirability of beta emitters, gamma emitters, others, or blends thereof, certain safety advantages are evident with the use of pure beta emitters over the more energetic gamma emitters. In general, the pure beta emitters have less energy, and exhibit a more limited penetration into tissue and deliver significantly less dose beyond the surface of the vessel wall. This probably requires close proximity of the radiation delivery source to the vessel wall, as is provided with the present invention, which may not be as necessary for the more deeply penetrating gamma emitters. Thus, although the present invention may be used for the delivery of gamma radiation, it is particular well adapted for the use of beta or other low energy emitters in view of the close proximity between the expanded flexible sheet 32 and the vessel wall.

Although optimization of a variety of radiation delivery parameters remains to be determined, such as ideal dose, dose delivery rate, cumulative dose, and activity among others, certain relationships are believed to be known at the present time and further optimization can be accomplished through routine experimentation by those of skill in the art.

For example, it appears that the cellular proliferation that follows balloon angioplasty has been localized to at least the media and likely the adventitia of the artery. Since the arterial wall of a diseased human coronary artery can easily exceed 2 millimeters thickness in an artery containing eccentric plaque, depth of penetration and proximity of the source to the wall become particularly important in a beta emitter treatment source. Thus, although beta emitters do not appear useful for the centered wire delivery devices, early clinical data incorporating beta emitters into stents adjacent the vessel wall appear promising. For example, experiments utilizing 7 millimeter length Palmaz-Schatz stents (Cordis, a Johnson & Johnson Company, Warren, N.J.) with activities ranging from 0.15–23.0 micro Ci of $_{32}P$. On histology at about 28 days following implantation into miniature swine, an encouraging dose response was observed. The neointima of the relatively high activity (3.0–23.0 mCi) stents included fibrin, erythrocytes, occasional inflammatory cells and smooth muscle cells with partial endothelialization of the luminal surface. The neointima of the low activity (0.15 and 0.5 mCi) stents was composed of smooth muscle cells and matrix with complete endothelialization of the luminal surface. Interestingly, in the 1.0 mCi stents, the neointima was expanded, consisting of smooth muscle cells and an abundant proteoglycan rich matrix. Thus, it appeared that at relatively low and high stent activities, within the range is tested, a significant reduction in the neointima and percent area stenosis may have occurred compared to the nonradioactive stents. See Tim A. Fischell M.D. and Andrew J. Carter, DO, Current Status of Radioactive Stents for the Prevention of In-Stent Restenosis, for the Scripps Coronary Interventions Course 1997.

Hehrlein et al., Radioactive Stent Implantation Inhibits Neointimal Proliferation in Non-Atherosclerotic Rabbits, Circulation 1995; 92:1570-5, reported activation of Palmaz-Schatz stents in a cyclotron, to produce beta and x-radiation as well as high energy gamma emitters in the stent. The radioactive stents were placed into rabbit iliac arteries and morphometric analysis at 4, 12 and 52 weeks demonstrated reduction of neointima formation compared to that obtained with conventional stents that were placed in the contra lateral arteries. Hehrlein et al. experimented with stents emitting $_{32}P$, and reported that the $_{32}P$ stents also inhibit neointima formation. However, only higher doses of 13 mCi demonstrated longetivity of the inhibitory effect at 12 weeks.

Laird et al., Inhibition of Neointimal Proliferation with Low Dose Irradiation From a Beta-Particle Emitting Stent, Circulation 1996; 93:529-36 used a $_{32}P$ impregnated Strecker stent at a low 0.14 mCi level of radioactivity in a porcine iliac model, and reported a 37% reduction in neointimal area and a 32% reduction in percent area stenosis for the beta particle emitting stents compared with control stents after 28 days. At four weeks following implantation, scanning electron microscopy revealed reendothelialization of the radioactive stents and no evidence of thrombosis.

In addition, a variety of theoretical calculations can be readily accomplished to provide guidance in clinical dosing optimization studies. For example, Janicki et al., Radiation Dose From a Phosphorous-32 Impregnated Wire Mesh Vascular Stent, Med. Phys 24:437-445; 1997, calculated a theoretical near field dose of a 1.0 mCi 15 millimeter length Palmaz-Schatz stent using a modification of the dose-point-kernel method. The calculation was modified to account for the geometry of a tubular slotted Palmaz-Schatz stent with mathematical modeling to take into account the differences from a uniform cylindrical distribution, to allow the generation of a theoretical dose distribution map. For a 1.0 Mci 15 millimeter length $_{32}P$ stent, at a distance of 0.1 millimeter dose values of about 2500 cGy are delivered at the strut wires and about 800 cGy between the wires over the 14.3 day $_{32}P$ half-life.

Calculations have also been accomplished using the higher energy yttrium 90 isotope for comparison. $^{90}Y$ has a 64-hour half-life and a maximal energy of 2.28 MeV, which is about 25% greater than $_{32}P$. Calculations have been reported based upon the use of a BX stent (Isostent Inc., San Carlos, Calif.) implanted with approximately 8–16 mCi of $^{90}Y$. The 15 millimeter BX stent would theoretically provide a dose rate of 40–100 cGy per hour at a distance of 0.5 millimeters from a the stent surface. The cumulative dose provided by an 8 to 16 mCi $^{90}Y$ stent would approximate 30–70 Gy over the lifetime of the isotope at a distance of 0.5 millimeters from the surface.

A variety of clinical studies are currently proposed or underway, to further optimize the dosing and isotope parameters, which can be readily incorporated into the delivery device of the present invention as will be well understood by those of skill in the art. Such studies involve the isotopes, among others, $^{90}Y$, $^{90}Sr/Y$, $_{32}P$, $^{186}Re$, and $^{192}Ir$.

The flexible sheet 32 can be activated to provide a radiation delivery source in any of a variety of ways as will be well understood in the art. For example, the metal sheet can be made radioactive such as by cyclotron activation, ion implantation, coating, and proton bombardment. Considering $_{32}P$ as an example, the metal sheet 32 can be made radioactive by ion implantation of $_3P$ beneath the metal surface followed by exposure to neutron irradiation. The neutron irradiation converts the $_{31}P$ into $_{32}P$. Alternatively, activation of a stainless steel flexible sheet 32 can be accomplished in a cyclotron.

Although the present invention has been described in terms of certain preferred embodiments, other embodiments will become apparent to those of ordinary skill in the art in view of the disclosure herein. Accordingly, the present invention is intended to be limited not by the specific disclosures herein, but solely by reference to the attached claims.

What is claimed is:

1. A radiation delivery catheter for temporarily placing a radioactive source adjacent a vessel wall, comprising:
   an elongate, flexible tubular body, having a proximal end and a distal end;
   an axially moveable core, having proximal and distal ends, extending through the tubular body; and
   at least one radioactive source in the form of a flexible radioactive sheet on the distal end of the core;
   wherein the radioactive sheet is moveable between a first position within the tubular body and a second position outside of the tubular body.

2. A catheter as in claim 1, wherein the radioactive sheet is rolled into a tube having a reduced diameter when in the first position, and the tube self expands by at least partially unrolling into a larger diameter adjacent the vessel wall when the sheet is in the second position.

3. A catheter as in claim 1, wherein the core further comprises a guidewire lumen extending therethrough.

4. A catheter as in claim 1, further comprising a guidewire lumen extending along at least a distal portion of the tubular body.

5. A catheter as in claim 1, further comprising an axially extending slot in the tubular body at the distal end thereof, for receiving the radioactive sheet.

6. A radiation delivery catheter as in claim 1, wherein the radioactive source has a thickness of no more than about 0.001 inches.

7. A radiation delivery catheter as in claim 1, wherein the radioactive source has a thickness of no more than about 0.0005 inches.

8. A radiation delivery catheter as in claim 1, wherein the radiation source comprises a beta emitter.

9. A radiation delivery catheter, comprising:
   a first elongate element, having a proximal end and a distal end;
   a second elongate element moveable with respect to the first element; and
   a radiation source attached to the second element, said radiation source having first and second ends;
   wherein rotation of the first end of the radiation source with respect to the second end causes the source to change from a reduced cross-sectional area to an enlarged cross-sectional area.

10. A radiation deliver catheter as in claim 9, wherein the radiation source comprises a flexible metal sheet.

11. A radiation delivery catheter as in claim 10, wherein the sheet is rolled into a first, reduced diameter tubular configuration for positioning at a treatment site in a vessel, and biased toward a second, larger diameter tubular configuration for expanding against the wall of the vessel.

12. A radiation delivery catheter as in claim 9, wherein the radiation source self expands from a reduced cross sectional profile to a larger cross sectional profile in response to axial movement of the second element with respect to the first element.

13. A radiation delivery catheter as in claim 9, wherein the radiation source is reducible from a relatively larger cross sectional area to a relatively smaller cross sectional area in response to rotation of the second element with respect to the first element.

14. A radiation delivery catheter as in claim 9, wherein the radiation source comprises a plurality of circumferentially extending elements.

15. A radiation delivery catheter, comprising:
   an elongate, flexible tubular body, having a proximal end and a distal end; and
   a self expandable circumferentially rolled radiation delivery source on the distal end of the delivery catheter.

16. A method of delivering a dose of radiation to a site in a vessel, comprising the steps of:
   providing a radiation delivery catheter having a self expandable radiation source on a distal end thereof,
   positioning the radiation source at the site; and
   permitting the radiation source to self expand at the site;

radially reducing the radiation source, and withdrawing the radiation source from the site;

wherein the permitting the radiation source to expand step comprises permitting at least one rolled flexible metal element to partially unroll from a reduced cross sectional area for positioning at the site to an enlarged cross sectional area for treating the site.

17. A method as in claim 16, wherein the radially reducing step comprises rolling the radiation source around a rotatable core wire.

18. A method of delivering a dose of radiation to a site in a vessel as in claim 16, wherein the positioning the radiation source step is accomplished following dilatation of the vessel wall at the site.

19. A method of delivering a dose of radiation to a site in a vessel as in claim 16, wherein the positioning the radiation source comprises positioning the source within a previously implanted stent.

20. A method of delivering a dose of radiation to a site in a vessel as in claim 16, wherein said permitting the radiation source to self-expand comprises permitting a plurality of adjacent elements to self-expand from a reduced profile rolled configuration to an enlarged tubular configuration to conform to the vessel wall throughout the axial length of the radiation source.

21. A method of delivering a dose of radiation to a site as in claim 16, further comprising the step of permitting the radiation source to deliver a dose of radiation to the vessel wall while in contact with the vessel wall prior to said radially reducing step.

22. A method as in claim 16, further comprising the step of permitting perfusion through the radiation source during a treatment period when the radiation source is in the enlarged cross sectional area configuration.

23. A method of delivering a dose of radiation to a site in a vessel, comprising the steps of:

providing a radiation delivery catheter having a thin sheet radiation source on a distal end thereof, positioning the radiation source at the site;

expanding the radiation source at the site;

radially reducing the radiation source, and withdrawing the radiation source from the site;

wherein the expanding the radiation source step comprises at least partially unrolling at least one rolled flexible sheet from a reduced cross sectional area for positioning at the site to an enlarged cross sectional area for treating the site.

24. A method as in claim 23, wherein the radially reducing step comprises rolling the radiation source around a rotatable core wire.

25. A method of delivering a dose of radiation to a site in a vessel as in claim 23, wherein the positioning the radiation source step is accomplished following dilatation of the vessel wall at the site.

26. A method of delivering a dose of radiation to a site in a vessel as in claim 23, wherein the positioning the radiation source comprises positioning the source within a previously implanted stent.

27. A method of delivering a dose of radiation to a site in a vessel as in claim 23, wherein said expanding step comprises permitting a plurality of adjacent elements to self-expand from a reduced profile rolled configuration to an enlarged tubular configuration to conform to the vessel wall throughout the axial length of the radiation source.

28. A method as in claim 23, further comprising the step of permitting perfusion through the radiation source during a treatment period when the radiation source is in the enlarged cross sectional area configuration.

29. A method of delivering radiation to a site in a vessel, comprising the steps of:

providing a radiation delivery source in the form of a thin sheet having a radioactive isotope thereon;

positioning the radiation delivery source at the site; and expanding the radiation delivery source at the site to bring the sheet into contact with the vessel wall;

wherein the expanding the radiation delivery source step comprises at least partially unrolling the sheet from a tubular roll having a reduced cross sectional area for positioning at the site to an enlarged cross sectional area for treating the site.

30. A method of delivering radiation to a site in a vessel as in claim 29, wherein said isotope is a beta emitter.

31. A method of delivering radiation to a site as in claim 29, wherein the thin sheet has a thickness of no more than about 0.001 inches.

32. A method of delivering radiation to a site as in claim 29, wherein the sheet has a thickness of no more than about 0.0005 inches.

33. A method of delivering radiation to a site as in claim 29, wherein said positioning step is accomplished following dilatation of the vessel at the site.

34. A method of delivering radiation to a site as in claim 29, wherein the positioning step comprises positioning the radiation delivery source within a previously implanted stent.

* * * * *